US005703263A

United States Patent [19]
Talley

[11] Patent Number: 5,703,263
[45] Date of Patent: Dec. 30, 1997

[54] PROCESS FOR MAKING CHIRAL ALPHA-AMINO PHOSPHONATES AND SELECTED NOVEL CHIRAL ALPHA-AMINO PHOSPHONATES

[75] Inventor: John J. Talley, Chesterfield, Mo.

[73] Assignee: Monsanto Company, St. Louis, Mo.

[21] Appl. No.: 408,237

[22] Filed: Mar. 22, 1995

Related U.S. Application Data

[62] Division of Ser. No. 163,017, Dec. 7, 1993, which is a division of Ser. No. 898,253, Jun. 15, 1992, Pat. No. 5,321,153.

[51] Int. Cl.$^6$ .................... C07F 9/40; C07F 9/38
[52] U.S. Cl. .................... 558/170; 558/172; 560/24; 560/29; 560/32; 562/75
[58] Field of Search .................... 558/170, 172; 562/15; 560/24, 29, 32

[56] References Cited

U.S. PATENT DOCUMENTS

| | | | |
|---|---|---|---|
| 4,016,148 | 4/1977 | Atherton et al. | 260/112.5 R |
| 4,277,420 | 7/1981 | Koenig | 560/24 |
| 4,316,847 | 2/1982 | Batcho et al. | 564/441 |
| 4,906,773 | 3/1990 | Taketami et al. | 562/570 |
| 4,912,221 | 3/1990 | O'Reilly et al. | 546/147 |
| 4,916,252 | 4/1990 | Sayo et al. | 560/39 |
| 4,939,288 | 7/1990 | Talley | 560/81 |
| 4,946,833 | 8/1990 | Lavielle et al. | 514/81 |

FOREIGN PATENT DOCUMENTS

| | | |
|---|---|---|
| 0207890 | 1/1987 | European Pat. Off. |
| 0375554 | 6/1990 | European Pat. Off. |
| 0409530 | 1/1991 | European Pat. Off. |
| 90352220/49 | 7/1990 | German Dem. Rep. |
| 90362221/49 | 7/1990 | German Dem. Rep. |
| 90362222/49 | 7/1990 | German Dem. Rep. |
| 870572083/09 | 10/1996 | German Dem. Rep. |
| 140-036 | 2/1980 | Germany |
| 4029444 | 3/1991 | Germany |
| 0032152 | 1/1991 | Japan |
| WO9200954 | 1/1992 | WIPO |

OTHER PUBLICATIONS

Asymmetric Synthesis of α-Aminophosphonates via Diastereoselective Addition of Lithium Diethyl Phosphite to Chelating Imines, Kraig M. Yager et al., J. Am. Chem. Soc., 1994, 116, 9377–9378.
Ewenson et al., "Int. J. Peptide Protein Res., 31" (1988) pp. 269–280.
Schollkoph et al., "Liebigs. Ann. Chem." (1985), 555–559.
Aboujaoude et al, "Phosphorus Sulfur" 1983, 18(1-2-3–) pp. 133–136 *Abstract Only*.
Chakravarty, P.K., et al., "J. Med. Chem", (1989), 32, pp. 1886–1890.
Ornstein, "J. Org. Chem." 1989, 54(9), pp. 2251–2252.
Sauveur et al. "Phosphorus Sulfur" 1983, 14(3), pp. 341–346 *Abstract Only*.
Growiak & Sawka-Dobrowelska, "Tetrahedron Letters" 1977, No. 45, pp. 3965–3968.
Parsons et al. "J. Med. Chem." (1988), No. 31, pp. 1772–1778.
Genet et al., "Tetrahedron Letters" (1986) vol. 27, No. 38, pp. 4573–4576.
Bavlis et al, "J. Chem. Soc. Perkin Trans I" (1984) 2845–2853.
Yuan and Oi "Synthesis" (1988) pp. 472–474.
Kukhar and Solodenko "Russ. Chem Rev.," (1987), pp. 859–874.
Dhawan and Redmore, "Phosphorus & Sulfur" (1987) 32, pp. 119–144.
Sawamura et al. "Tetrahedron Letters" (1989) vol. 30, No. 17 pp. 2247–2250.
Sting and Steglich, "Synthesis" (1990) February, pp. 132–134 *Abstract Only*.
Solodenko et al "Tetrahedron" (1991) vol. 47, No. 24, pp. 3989–3998.
Kafarski and Lejczak, "Can. J. Chem." (1983), 61, pp. 2425–2430.
Atherton et al, "Antimicrobial Agents and Chemotherapy" (1979) pp. 677–683.
Atherton et al "J. Med. Chem" (1986) 29, pp. 29–40.
Scholkoph and Schultz "Liebigs Ann. Chem" (1987) pp. 45–49.
Bartlett and Lamden "Bioorganic Chemistry" (1986) 14, pp. 356–377.
Huber and Vasella "Helvetica Chimica Acta" (1987), 70, pp. 1461–1476.
Petrov, K.A., Chauzov, V.A., Erokhina, T.S. "Russ Chem. Rev." (1974) 43, p. 984.
Atherton, F.R., Hall, M.J., Hassal, C.H., Lambert, R.W., Llod, W.J., Ringro P.S. "Antimicrob. Agents Chemother", 1979, 15, 696.
Schollkopf et al., Liebigs Ann. Chem., (3), pp. 555–559 (1985).

*Primary Examiner*—Gary Geist
*Assistant Examiner*—Barbara S. Frazier
*Attorney, Agent, or Firm*—Fitzpatrick, Cella, Harper & Scinto

[57] ABSTRACT

This invention is selected novel chiral (essentially pure) alpha-amino phosphonates, process for the preparation which is a catalytic asymmetric hydrogenation of olefins and novel intermediates therefor. The alpha-amino phosphonates are useful as antibiotics and/or as intermediates in the preparation of phosphorus-containing analogs of peptides, i.e., phosphonopeptides or pseudopeptides having known uses, such as in antibiotics, antibiotic enhancers, or enzyme inhibitors.

9 Claims, No Drawings

PROCESS FOR MAKING CHIRAL ALPHA-AMINO PHOSPHONATES AND SELECTED NOVEL CHIRAL ALPHA-AMINO PHOSPHONATES

This application is a divisional of U.S. application Ser. No. 08/163,017 filed Dec. 7, 1993, now pending, which is a division of U.S. application Ser. No. 07/898,253 filed Jun. 15, 1992, now U.S. Pat. No. 5,321,153 issued Jun. 14, 1994.

BACKGROUND OF THE INVENTION

The present invention relates to catalytic asymmetric hydrogenation of olefins to synthesize chiral alpha-amino phosphonates and selected novel chiral alpha-amino phosphonates. The chiral alpha-amino phosphonates are either useful as biocides, antibiotics and/or useful in the preparation of phosphorus-containing analogs of peptides, i.e., phosphono peptides or pseudopeptides having known uses. For example, such phosphorus-type compounds have been shown to be effective as antibiotics, antibiotic enhancers, or enzyme inhibitors.

In the past desired stereoisomers have been difficult to obtain. Laborious and expensive processes such as those using fractional crystallization and recycle loops have been common in procedures involving a resolution step to obtain a desired stereoisomer. More recently some olefins have been subjected to asymmetric hydrogenation over rhodium and other metal coordination catalysts having optically active ligands.

Such asymmetric hydrogenation for the preparation of selected enantiomers is shown by the following references:
U.S. Pat. No. 4,939,288;
U.S. Pat. No. 4,377,420;
East German Application Nos. 280,527; 280,528; 280,529; 340,372 described in corresponding Derwent Abstract Numbers 90-362220/49, 90-362221/49, 90-362222/49, 87-057083/09, respectively;
Int. J. Peptide Protein Res. 41, 1988, 269–280;
U.S. Pat. No. 4,912,221;
EP Application No. 90307750.1;
U.S. Pat. No. 4,906,773;
U.S. Pat. No. 4,916,252;
U.S. Pat. No. 4,316,847;
EP Application No. 89403599.7;
Japanese Number 3002152A described in WPI Acc No. 91-048825;
German Appl. No. 140-036 described in Derwent Abstract No. 34661C/20.1

Some (1-Aminoalkyl)phosphonic acids, the phosphonic acid analogs of amino acids, and particularly the selected enantioselective synthesis of optically pure aminophosphonic acids and phosphonopeptides have been prepared by resolution and by asymmetric synthesis using chiral auxiliaries. This is exemplified by the following references:
Schollkoph et al, *Liebigs Ann. Chem.*, 1985, 555–559;
Aboujaoude et al, *Phosphorus Sulfur*, 1983, 18(1–2–3), pp. 133–6;
Bissane et al, *Pept. 1990 Proc. Eur. Pept. Symp. 21st*, Meeting Date 1990-9;1990, pp. 438–9,
Glowak et al, *Khim. Primen. Fosfororg. Soedin., Tr. Yubileinoi Kong., 6th Meeting Date 1977*, 1981, pp.2251–3;
Ornstein, *J. Org. Chem.*, 1989, 54(9), pp. 2251–2;
Sauveur et al, *Phosphorus Sulfur*, 1983, 14(3), pp. 341–6;
Growiak and Sawka-Dobrowolska, *Tetrahedron Letters*, 1977, No. 45, pp. 3965–8; and
Parsons et al, *J. Med. Chem.* 1988, No. 31, pp. 1772–8.

Schollkoph et al report that "attempts to hydrogenate 3a" (which is N-[1-(dimethoxyphosphoryl)-ethenyl]formamide) at room temperature, normal pressure) in the presence of (R,R)-DIPAMP failed." Schollkoph et al disclose the reduction of certain dehydro alpha-amino phosphonates by catalytic asymmetric hydrogenation in the presence of rhodium (+) DIOP catalyst. Thus, surprisingly, both the chemical yield and the asymmetric induction providing enantiomeric enhancements (ee) of the present invention process provide essentially pure compounds of a particular stereoisomeric form including selected chiral compounds now essentially pure not previously known. Further, Genet et al, *Tetrahedron letters*, 1986, Vol. 27, No. 38, pp 4573–76, provide comparisons of DIOP and DIPAMP in a different asymmetric allylation consistent with Schollkoph.

Reported diastereomeric mixtures of 1-aminoalkylphosphono type compounds are found in numerous references of which the following are examples:
Baylis et al, *J. Chem. Soc. Perkin Trans 1* 1984, 1984, 2845–53;
Yuan and Qi, *Synthesis*, 1988, June, 472–4 disclose 1-amino-substituted benzyl phosphonic acids where the benzyl includes various substituents.
U.S. Pat. No. 4,016,148 discloses peptide derivatives having a moiety characterized by the replacement of the carboxyl group of a naturally occurring L alpha-amino acid by a phosphorus group including a —$P(O)(OH)_2$ group.

Recent reviews disclosing the preparation of selected diastereomeric and chiral alpha-amino phosphonates are found in the following references respectively:
Kukhar and Sclodenko, *Russ. Chem. Rev.*, 1987, pp. 1504–32; and
Dhawan and Redmore, *Phosphorus and Sulfur*, 1987, 32, pp. 119–44.

The following additional references disclose various specific chiral alpha-amino phosphonates:
Sawamura et al, *Tetrahedron Letters*, 1989, Vol. 30, No. 17, pp 2247–50;
Sting and Steglich, *Synthesis*, 1990, February, pp. 132–4;
Solodenko et al, *Tetrahedron*, 1991, Vol. 47, No. 24, pp. 3989–98;
Kafarski and Lejczak, *Can. J. Chem.* 1983, 61, pp. 2425–30;
Atherton et al, *Antimicrobial Agents and Chemotherapy*, 1979, May, pp. 677–83;
Atherton et at, *J. Med. Chem.*, 1986, 29, pp. 29–40;
Scholkoph and Schutze, *Liebigs Ann. Chem.*, 1987, pp. 45–9;
Bartlett and Lamden, *Bioorganic Chemistry*, 1986, 14, pp. 356–77;
Huber and Vasella, *Helvetica Chimica Acta*, 1987, 70, pp. 1461–76.

The interesting biological properties of α-aminophosphonates make them attractive analogues of α-amino acids, [(a) Redmore, D. *Top. Phosphorus Chem.*, 1976, 8, 515; (b) Petroy, K. A.; Chauzov, V. A.; Erokhina, T. S. *Russ. Chem. Rev.* 1974, 43, 984; (c) Kafarski, P.; Mastarlerz, P. *Aminophosphonates: Natural Occurance, Biochemistry and Biological Properties*, Bertrage zur Wirkstofforschung, Ak. Ind. Kompl. DDR, 1984, 21.] While they resemble their carbon counterparts, the tetrahedral phosphorus also allows them to function as transition state analogues. These pharmaceutically-interesting compounds [Certain phosphorus analogues of α-amino phosphonates are being investigated by the pharmaceutical industry as antibiotics, see; (a) Atherton, F. R.; Hall, M. J.; Hassall, C. H.; Lambert, R. W.; Llod, W. J.; Ringrose, P. S. *Antimicrob.*

*Agents Chemother.*, 1979, 15, 696; (b) Chakravarty, P. K.; Greenlee, W. J.; Parsons, W. H.; Patchett, A. A.; Combs, P.; Roth, A.; Busch, R. D.; Mellin, T. N. *J. Med. Chem.*, 1989, 32, 1886 and references therein.] have been synthesized by various racemic routes, but the need to develop a practical asymmetric method still exists. The present invention now successfully fulfills this need.

α-Amino phosphonates have recently been reported to serve as starting materials for the preparation of potent inhibitors of HIV-1 protease. (Dreyer, G. B. *New diamino phosphinic acid derivatives are aspartic protease inhibitors used to treat viral infections especially HIV type* 1. Patent Application W09200954-A1, Jan. 20, 1992, assigned to SmithKline Beecham Corp.) This application is incorporated herein by reference to provide the basis for utility for the present invention process and its intermediates. Since the α-amino phosphonate employed by Dreyer et al was racemic (Dreyer, G. B.; Choi, J. K.; Meek, T. D.; Tomaszek, T. A., Jr. 203rd American Chemical Society Meeting, San Francisco, Calif. April 5–10, 1992, Medicinal Chemistry #179), the inhibitor was made as a mixture of isomers necessitating a tedious chromatographic separation in order to isolate the most active constituent. The most active isomer was derived from the phosphorus analogue of phenylalanine with the L(R) absolute configuration. Not only would the methodology described herein be adaptable to the preparation of the most active isomer of the SKB HIV-protease inhibitor, but to a wide variety of analogues as well. Intermediates of U.S. Pat. No. 4,946,833 and each of European Application Nos. 89401595.7 and 90402226.6 are related to the novel compound I of the present invention. German Application 4029444A abstracted in Derwent Abstract No. 91-095191/14 discloses compounds for regulating plant growth related to the novel compounds of Formula II of the present invention. Further, EP 207,890A disclosed in Derwent Abstract No. 87-001565/01 includes 1-amino-2-phenyl-ethylphosphorus acid derivatives as microbiocidal and biocidal agents.

The flexibility of the present synthesis permits the synthesis of very unique analogues of α-amino phosphonates that are related to known compounds having biological properties relative to molecules available by more demanding syntheses. The literature is replete with examples of novel amino acid side chains designed to impart improved biological properties to analogous molecules.

BRIEF SUMMARY OF THE INVENTION

The present invention is a novel compound of the formula (I)

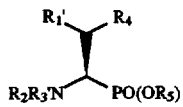

wherein $R_1'$ is
(1) cyclopentyl, cyclopentylmethyl, cyclohexyl, or cyclohexylmethyl;
(2) alkyl of from one to six carbons substituted by one or two hydroxyl, chloro, or fluoro;
(3) phenyl substituted by one to three substituent(s) consisting of
   (a) halogen consisting of fluoro, chloro, bromo, iodo,
   (b) alkoxy of from one to three carbons,
   (c) nitro,
   (d) amido,
   (e) mono- or di- alkyl (of from one to four carbons) amido;
   (f) hydroxy with the proviso that when the substituent is one or two hydroxy then one of hydroxy can not be in the position para to the phenyl bond,
(4) tolyl;
(5) tolyl substituted by one to three substituents consisting of
   (a) alkyl of from one to four carbons,
   (b) halogen consisting of fluoro, chloro, bromo, iodo,
   (c) alkoxy of from one to three carbons,
   (d) nitro,
   (e) amido,
   (f) mono- or di- alkyl (of from one to four carbons) amido;
   (g) hydroxy;
(6) naphthyl optionally attached through a $CH_2$ group and optionally substituted by one to three substituents consisting of
   (a) alkyl of from one to four carbons,
   (b) halogen consisting of fluoro, chloro, bromo or iodo,
   (c) alkoxy of from one to three carbons,
   (d) nitro,
   (e) amido,
   (f) mono- or di- alkyl (of from one to four carbons) amido,
   (g) hydroxy; or
(7) indol-3-yl, indol-2-yl, or imidazol-4-yl, or indol-3-ylmethyl, indol-2-ylmethyl or imidazol-4-ylmethyl;
(8) NHA wherein A is
   (a) trityl,
   (b) hydrogen,
   (c) alkyl of from one to six carbons,
   (d) $R_{10}CO$ wherein $R_{10}$ is (A)hydrogen, (B) alkyl of from one to three carbons optionally substituted with hydroxyl, chloro, or fluoro, (C) phenyl or naphthyl; unsubstituted or substituted with one to three of (i) alkyl of from one to three carbons, (ii) halogen where halogen is F, Cl, Br, or I, (iii) hydroxy, (iv) nitro, (v) alkoxy of from one to three carbons, (vi) $CON(R_{11})_2$ wherein $R_{11}$ is independently hydrogen or alkyl of from one to four carbons, or (D) a 5 to 7 member heterocycle such as indolyl, pyridyl, furyl or benzisoxazolyl;
   (e) phthaloyl wherein the aromatic ring is optionally substituted by one to three of (A) alkyl of from to three carbons, (B) halogen where halogen is F, Cl, Br, or I, (C) hydroxy, (D) nitro, (E) alkoxy of from one to three carbons, (F) $CON(R_{11})_2$ wherein $R_{11}$ is independently hydrogen or alkyl of from one to four carbons,
   (f) $R_{12}(R_{13}R_{14}C)_m CO$ wherein m is one to three and $R_{12}, R_{13}$, and $R_{14}$ are independently (A) hydrogen, (B) chloro or fluoro, (C) alkyl of from one to three carbons optionally substituted by chloro, fluoro, or hydroxy, (D) hydroxy, (E) phenyl or naphthyl optionally substituted by one to three of (i) alkyl of from to three carbons, (ii) halogen where halogen is F, Cl, Br, or I, (iii) hydroxy, (iv) nitro, (v) alkoxy of from one to three carbons, (vi) $CON(R_{11})_2$ wherein $R_{11}$ is independently hydrogen or alkyl of from one to four carbons, (F) alkoxy of from one to three carbons, (G) 5 to 7 member heterocycle such as indolyl, pyridyl, furyl, or benzisoxazolyl, or (H) $R_{12}, R_{13}$, and $R_{14}$ are independently joined to form a monocyclic, bicyclic, or tricyclic ring system each ring of which is a cycloalkyl of from three to six carbons; except that only one of $R_{12}$, $R_{13}$ and $R_{14}$ can be hydroxy or alkoxy on the same carbon and can not be hydroxy, chloro or fluoro when m is one;

(g) $R_{12}(R_{13}R_{14}C)_m W$ wherein m is independently 1 to 3 and W is OCO or $SO_2$ and $R_{12}$, $R_{13}$ and $R_{14}$ are independently as defined above;

(h) $R_{20}W$ wherein $R_{20}$ is a 5 to 7 member heterocycle such as indolyl, pyridyl, furyl, or benzisoxazolyl;

(i) $R_{21}W$ wherein $R_{21}$ is phenyl or naphthyl; unsubstituted or substituted by one to three substituents of (i) alkyl of from one to three carbons, (ii) halogen where halogen is F, Cl, Br, or I, (iii) hydroxy, (iv) nitro, (v) alkoxy of from one to three carbons, (vi) $CON(R_{11})_2$ wherein $R_{11}$ is independently hydrogen or alkyl of from one to four carbons;

(j) $R_{12}(R_{13}R_{14}C)_m P(O)(OR_{22})$ wherein $R_{22}$ is alkyl of from one to four carbons or phenyl and $R_{12}$, $R_{13}$ and $R_{14}$ are independently as defined above;

(k) $R_{20}P(O)(OR_2)$ wherein $R_{20}$ and $R_{22}$ are as defined above;

(l) $R_{21}R(O)(OR_{22})$ wherein $R_{21}$ and $R_{22}$ as defined above;

(9) $R_{12}(R_{13}R_{14}C)_m V$ wherein V is O or NH and $R_{12}$, $R_{13}$ and $R_{14}$ are independently as defined above;

(10) $N(R_{11})_2$ wherein $R_{11}$ is independently as defined above;

(11) $NR_{15}NR_{16}$ wherein $R_{15}$ and $R_{16}$ are joined to form a 4 to 6 membered saturated nitrogen containing heterocycle which is (i) azetidinyl, (ii) pyrrolidinyl, (iii) piperidinyl, or (iv) morpholinyl;

(12) $R_{17}OCH_2O$ wherein $R_{17}$ is
 (a) alkyl of from one to six carbons,
 (b) $R_{21}$ wherein $R_{21}$ is independently defined as above; or
 (c) $CH_2Q_1$ wherein $Q_1$ is phenyl, naphthyl or a 5 to 7 membered heterocycle independently as defined above;

(13) $R_{17}OCH_2CH_2OCH_2$ wherein $R_{17}$ is independently as defined above;

(14) alkynyl of from two to six carbons optionally substituted with $R_{21}$ where in $R_{21}$ is independently as defined above;

(15) alkenyl of from two to six carbons optionally substituted with $R_{21}$ where in $R_{21}$ is independently as defined above;

$R_2$ and $R_5$ are independently hydrogen, alkyl, lower cycloalkyl, or ar wherein ar is an aromatic group, preferably unsubstituted or substituted phenyl;

$R_3'$ is hydrogen, an amino acid radical or a protecting group such as a substituted or unsubstituted acyl; and $R_4$ is hydrogen and with the proviso that when $R_3'$ is hydrogen, then $R_1'$ cannot be (1) alkyl substituted by hydroxy, (2) phenyl substituted by halogen, hydroxy or alkoxy, (3) 2-indolyl, (4) 4-imidazolyl, or (5) alkoxycarbonyl.

The present invention is also a compound of the formula (II)

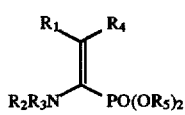

wherein $R_1$, $R_2$, $R_3$, $R_4$ and $R_5$ are all as defined herein.

The present invention is also a process comprising the treatment of a compound of the formula (II)

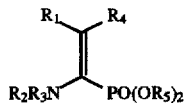

wherein $R_1$ is
(1) hydrogen;

(2) alkyl of from 1 to 6 carbons optionally substituted by one or two hydroxyl, chloro or fluoro;

(3) cycloalkyl of from 3 to 7 ring carbons;

(4) $ar_4$ which is a group such as phenyl, or phenyl substituted by one to three substituent(s) consisting of
 (a) alkyl of from one to four carbons,
 (b) halogen consisting of fluoro, chloro, bromo, iodo,
 (c) alkoxy of from one to three carbons,
 (d) nitro,
 (e) amido,
 (f) mono- or di- alkyl (of from one to four carbons) amido;
 (g) hydroxy;

(5) $ar_5$ which is a group such as tolyl;

(6) $ar_6$ which is a group such as tolyl substituted by one to three substituents consisting of
 (a) alkyl of from one to four carbons,
 (b) halogen consisting of fluoro, chloro, bromo, iodo,
 (c) alkoxy of from one to three carbons,
 (d) nitro,
 (e) amido,
 (f) mono- or di- alkyl (of from one to four carbons) amido,
 (g) hydroxy;

(7) $ar_7$ which is a group optionally attached through a $CH_2$ and is naphthyl or naphthyl substituted by one to three substituents consisting of
 (a) alkyl of from one to four carbons,
 (b) halogen consisting of fluoro, chloro, bromo, iodo,
 (c) alkoxy of from one to three carbons,
 (d) nitro,
 (e) amido,
 (f) mono- or di- alkyl (of from one to four carbons) amido,
 (g) hydroxy; or (8) $ar_8$ which is a group such as indol-3-yl, indol-2-yl, or imidazoly-4-yl or indol-3-ylmethyl, indol-2-ylmethyl or imidazol-4-ylmethyl (preferably unsubstituted or substituted phenyl or indol-3-yl);

(9) NHA wherein A is
 (a) trityl,
 (b) hydrogen,
 (c) alkyl of from one to six carbons,
 (d) $R_{10}CO$ wherein $R_{10}$ is (A)hydrogen, (B) alkyl of from one to six carbons optionally substituted with hydroxyl, chloro, or fluoro, (C) phenyl or naphthyl unsubstituted or substituted with one to three of (i) alkyl of from one to three carbons, (ii) halogen where halogen is F, Cl, Br, or I, (iii) hydroxy, (iv) nitro, (v) alkoxy of from one to three carbons, (vi). $CON(R_{11})_2$ wherein $R_{11}$ is independently hydrogen or alkyl of from one to four carbons, or (D) a 5 to 7 member heterocycle such as indolyl, pyridyl, furyl or benzisoxazolyl;
 (e) phthaloyl wherein the aromatic ring is optionally substituted by one to three of (A) alkyl of from one to three carbons, (B) halogen where halogen is F, Cl, Br, or I, (C) hydroxy, (D) nitro, (E) alkoxy of from one to three carbons, (F) $CON(R_{11})_2$ wherein $R_{11}$ is independently hydrogen or alkyl of from one to four carbons,
 (f) $R_{12}(R_{13}R_{14}C)_m CO$ wherein m is one to three and $R_{12}, R_{13}$, and $R_{14}$ are independently (A) hydrogen, (B) chloro or fluoro, (C) alkyl of from one to three carbons optionally substituted by chloro, fluoro, or hydroxy, (D) hydroxy, (E) phenyl or naphthyl optionally substituted by one to three of (i) alkyl of from to three carbons, (ii)

halogen where halogen is F, Cl, Br, or I, (iii) hydroxy, (iv) nitro, (v) alkoxy of from one to three carbons, (vi) $CON(R_{11})_2$ wherein $R_{11}$ is independently hydrogen or alkyl of from one to four carbons, (F) alkoxy of from one to three carbons, (G) 5 to 7 member heterocycle such as indolyl, pyridyl, furyl, or benzisoxazolyl, or (H) $R_{12}, R_{13}$, and $R_{14}$ are independently joined to form a monocyclic, bicyclic, or tricycle ring system each ring of which is a cycloalkyl of from three to six carbons; except that only one of $R_{12}$, $R_{13}$ and $R_{14}$ can be hydroxy or alkoxy on the same carbon and can not be hydroxy, chloro or fluoro when m is one;

(g) $R_{12}(R_{13}R_{14}C)_mW$ wherein m is independently 1 to 3 and W is OCO or $SO_2$ and $R_{12}, R_{13}$, and $R_{14}$ are independently as defined above;

(h) $R_{20}W$ wherein $R_{20}$ is a 5 to 7 member heterocycle such as pyridyl, furyl, or benzisoxazolyl;

(i) $R_{21}W$ wherein $R_{21}$ is phenyl or naphthyl; unsubstituted or substituted by one to three substituents of (i) alkyl of from one to three carbons, (ii) halogen where halogen is F, Cl, Br, or I, (iii) hydroxy, (iv) nitro, (v) alkoxy of from one to three carbons, (vi) $CON(R_{11})_2$ wherein $R_{11}$ is independently hydrogen or alkyl of from one to four carbons;

(j) $R_{12}(R_{13}R_{14}C)_mP(O)(OR_{22})$ wherein $R_{22}$ is alkyl of from one to four carbons or phenyl and $R^{12}$, $R_{13}$ and $R_{14}$ are independently as defined above;

(k) $R_{20}P(O)(OR_{22})$ wherein $R_{20}$ and $R_{22}$ are as defined above;

(l) $R_{21}P(O)(OR_{22})$ wherein $R_{21}$ and $R_{22}$ are as defined above;

(10) $R_{12}(R_{13}R_{14}C)_mV$ wherein V is O or NH and $R_{12}$, $R_{13}$ and $R_{14}$ are independently as defined above;

(11) $N(R_{11})_2$ wherein $R_{11}$ is independently as defined above;

(12) $NR_{15}NR_{16}$ wherein $R_{15}$ and $R_{16}$ are joined to form a 4 to 6 membered saturated nitrogen containing heterocycle which is (i) azetidinyl, (ii) pyrrolidinyl, (iii) piperidinyl, or (iv) morpholinyl;

(13) $R_{17}OCH_2O$ wherein $R_{17}$ is
 (a) alkyl of from one to six carbons,
 (b) $R_{21}$ wherein $R_{21}$ is independently defined as above; or
 (c) $CH_2Q_1$ wherein $Q_1$ is phenyl, naphthyl or a 5 to 7 membered heterocycle as defined above;

(14) $R_{17}OCH_2CH_2OCH_2$ wherein $R_{17}$ is independently as defined above;

(15) alkynyl of from two to six carbons optionally substituted with $R_{21}$ where in $R_{21}$ is independently as defined above;

(16) alkenyl of from two to six carbons optionally substituted with $R_{21}$ where in $R_{21}$ is independently as defined above;

$R_2$ and $R_5$ are independently hydrogen, alkyl, lower cycloalkyl, or an aromatic group, preferably unsubstituted or substituted phenyl;

$R_3$ is a protecting group such as a substituted or unsubstituted acyl; and $R_4$ is hydrogen or lower cycloalkyl; with the overall proviso that one of $R_1$ and $R_4$ must be hydrogen;

with hydrogen in the presence of rhodium (R,R)-(1,2-ethanediyl bis[(orthomethoxyphenyl) phenylphosphine] ($H_2RhDiPAMP$) in a deoxygenated solvent; optionally (1) deprotecting the nitrogen or (2) deprotecting the nitrogen and further treating to add an amino acid radical to the nitrogen, to obtain a compound of the formula (I)

wherein $R_1$, $R_2$, $R_4$ and $R_5$ is as defined above; and $R_3'$ is hydrogen, amino acid radical or a protecting group.

The present invention is also the process comprising the condensation of a compound of the formula (III)

wherein $R_1$ is as defined above with a compound of the formula (IV)

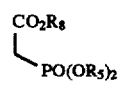

wherein $R_5$ is as defined and $R_8$ is a protecting group; in the presence of titanium tetrachloride; to obtain a compound of the formula (V and VA)

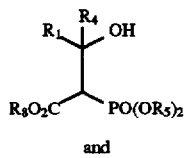

and

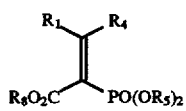

and then V and VA are treated with a solution of trifluoroacetic acid in an inert solvent such as methylene chloride in the presence of molecular sieves to obtain the mixture of the formula (VI and VIA)

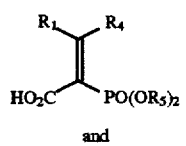

and

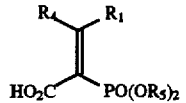

which is treated with diphenylphosphoryl azide at about 0° C., extracted and warmed to effect Curtius rearrangement; and treated with an alcohol, such as para-methoxybenzyl alcohol, tert-butyl alcohol or benzyl alcohol or the like, to trap the incipient isocyanate and to obtain compound of the formula (II)

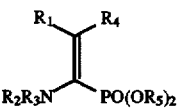

wherein $R_1$, $R_2$, $R_3$, $R_4$ and $R_5$ are as defined above.

Optionally this immediately preceding process to obtain the compound II may also include a further step wherein the compound of formula II is further treated with hydrogen in the presence of rhodium (R,R)-(1,2-ethanediyl bis[(orthomethoxyphenyl)phenylphosphine] in a deoxygenated solvent; and optionally (1) treated to deprotect the nitrogen, (2) and to add an amino acid radical on the nitrogen to obtain a compound of the formula (I)

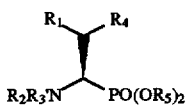

wherein $R_1$, $R_2$, $R_3'$, and $R_5$ is as defined above.

The preferred process is for the preparation of the phosphorus analog of L-phenylalanine.

DETAILED DESCRIPTION OF THE INVENTION

The terms in the present invention generally have the following meaning.

Alkyl means an alkyl of from one to six carbons such as methyl, ethyl, propyl and the like and isomers thereof.

An aromatic group means a phenyl, substituted phenyl, tolyl, substituted tolyl, naphthyl, indol-3-yl, indol-2-yl, a 5 to 7 membered heterocycle group such as pyridyl, furyl, or benzisoxazolyl and the like. The latter heterocyclic group is usually attached through one of the carbon atoms of the ring.

Substituted phenyl and substituted tolyl means each of phenyl or tolyl is substituted with from one to three substituents such as alkyl, carboxyl, hydroxyl (and base salts thereof), alkoxy, halogen, acyloxy, aryloxy, aralkoxy, amino, alkyl amido (both mono and di alkylamido), nitro, cyano or sulfonyl.

Acyl means such groups as acetyl, benzoyl, formyl, propionyl, butyryl, toluyl, and may include substituted such groups, for example nitrobenzoyl, and the like; and may also include groups composing urethano groups with the nitrogen, such as carbalkoxy groups, for example, carbethoxy, and the like or other acyl variants commonly used as blocking groups in peptide synthesis. In other words the blocking groups in the present invention are commonly acyl groups.

Lower cycloalkyl means cyclic hydrocarbon groups containing 3 to 6 carbon atoms, such as cyclopropyl, cyclobutyl, cyclopentyl, cyclohexyl.

The compounds and the processes of the present invention include an asymmetric carbon adjacent to the carbon on which the nitrogen and phosphorus group are attached. In the compound of the formula I or of the compound of the formula I' the stereo configuration of this carbon is the same as the carbon in an analogous naturally occurring peptide configuration and is essentially optically pure. In other words the present invention provides a novel synthesis for obtaining optically pure compounds and selected novel optically pure compounds of the synthesis corresponding to an analogous naturally occurring peptide.

Consequently, an ordinarily skilled artisan can determine pharmacological activity for selected compounds within the formula I' and also ascertain the usual and customary dosage forms or dosages by the use of analogous means as applied to the naturally occurring peptide.

Likewise use of the compounds of the formula I as intermediates in the preparation of compound which are derivatives of the compounds of formula I are also within the skill of the ordinary artisan.

The compounds of the invention may contain other isomeric moieties within its substituents. Thus, the invention includes the individual isomers and mixtures thereof. The individual isomers of this type may be prepared or isolated by methods known in the art.

Chiral means optically active.

The compounds of Formula I' which manifest pharmacologically activity are useful both in the free base and the free acid form or in the form of base salts thereof, as well as, in the form of acid addition salts. All forms are within the scope of the invention. In practice, use of the salt form amounts to use of the free acid or free base form. Appropriate pharmaceutically acceptable salts within the scope of the invention are those derived from mineral and organic acids or those derived from bases such as suitable organic and inorganic bases. For example, see "Pharmaceutical Salts", *J. Pharm. Sci.*, 66(1), 1–19 (1977). The acid addition salts of said compounds are prepared either by dissolving the free base of compound I' in aqueous or aqueous alcohol solution or other suitable solvents containing the appropriate acid or base and isolating the salt by evaporating the solution, or by reacting the free base of Compound I" having an acid group thereon with a base such that the reactants are in an organic solvent, in which case the salt separates directly or can be obtained by concentration of the solution.

The base salts of compounds of Formula I described above are prepared by reacting the appropriate base with a stoichiometric equivalent of the acid compounds of Formula I to obtain pharmacologically acceptable base salts thereof.

Specifically, the present invention is a process as shown in Scheme 1.

The process of Scheme 1 may generally be carried out at from about 1 to 100 psig and at a temperature from about 0° C. to 60° C., preferably at about room temperature and at a pressure about 40 psig, in inert solvents such as methanol, ethanol, tetrahydrofuran, dichloromethane, acetonitrile and the like or mixtures thereof.

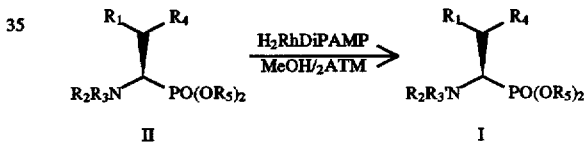

Evaluation of the results may be accomplished by standard methods, such as vapor phase chromatography on a chiral capillary column, or by HPLC (high performance liquid chromatography) on a chiral column or by evaluation of the optical rotation of a solution of the compound.

More particularly the process of Scheme 1 may be accomplished be the following general procedure.

A Fisher-Porter bottle is charged with the appropriate substrate II dissolved in deoxygenated methanol along with 0.1–1.0 mol percent rhodium (R, R)-DiPAMP (R,R)-(1,2-ethanediyl bis[(o-methoxyphenyl)phenylphosphine]. After 5 nitrogen purges (40 psig) the solution was purged 5 times with hydrogen (40 psig) and then allowed to hydrogenate at room temperature for 1–24 h. The hydrogen was replaced with nitrogen and the contents of the bottle concentrated in vacuo. The catalyst residue was separated from the chiral alpha-amino phosphonate I by dissolving the product in iso-octane. The catalyst residue is not soluble in iso-octane.

A general procedure for the hydrolysis of chiral N,O-protected alpha-amino phosphonates of the formula I wherein $R_3'$ is a protecting group is as follows. A sample of the chiral N,O-protected alpha-amino phosphonate derivative is refluxed for 24 h with 12N hydrochloric acid. The solvent is removed in vacuo. The residue is taken up in water and re-concentrated in vacuo. After thoroughly drying under vacuum the hydrochloride salt is converted to the free amine by treatment with excess propylene oxide. The precipitated amino acid is then isolated by filtration and optionally recrystallized from water/methanol.

An evaluation is made of optical purity by chiral vapor phase chromatography. The N,O-protected chiral alpha-amino phosphonate derivatives are analyzed by chiral gas chromatography for optical purity. A solution of the racemic amino acid derivative in dichloromethane is separated into the two enantiomers by a 25 meter Chirasil Val III capillary column with flame ionization detection. After conditions for separation of the two enantiomers are established, each chiral hydrogenation product is evaluated for the extent of optical purity.

Specifically, when $R_1$ is hydrogen and; $R_3$ is $C_6H_5CH_2OCO$ in the above described hydrogenation of the compound of the formula II at 40 psig in methanol at room temperature gives the product of the formula I wherein $R_1$ is hydrogen and $R_2$ is $C_6H_5CH_2OCO$ in a yield of 98% after two hours and evaluation of the optical purity of the compound of the formula I by vapor phase chromatography on a chiral capillary column revealed that the L-isomer was formed to the extent of 95% purity.

Variations in these conditions and evaluations for different compounds within the definitions of the formula I are within the skill of an ordinarily skilled artisan.

The compounds of the formula II are known or can be prepared from compounds that are known by methods known in the art or for compounds of the above formula II can be prepared by the following methods.

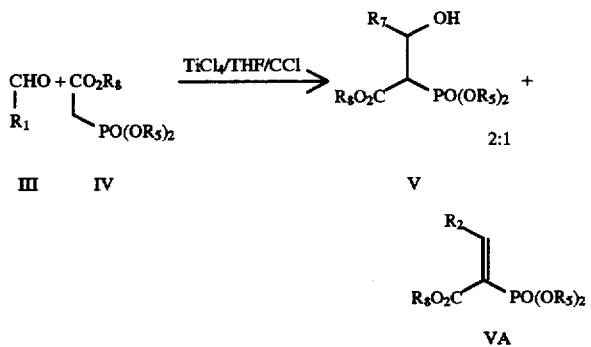

Condensation of the compound of the formula III with the compound of the formula IV in the presence of titanium tetrachloride gives the expected Knovenagel, (Lehnert, W., Tet. Lett., 1970 pp. 4723–4; Lehnert, W., Tetrahedron, 1973, 29, pp. 635–8), product along with the aldol condensation product in good yield (V and VA). Treatment of this mixture with a solution of trifluoroacetic acid in methylene chloride in the presence of molecular sieves results in dehydration and the formation of a 3:1 mixture of Z:E isomers (VI and VIA). Treatment of this mixture with diphenylphosphoryl azide at about 0° C. followed by extractive work-up gives the corresponding acyl azide. The acyl azide is then diluted with toluene and warmed to 90° C. to effect Curtius rearrangement. The incipient isocyanate is then trapped in situ with benzyl alcohol to produce the corresponding N-protected dehydro alpha-amino phosphonate of the formula II as a single (E) geometrical isomer.

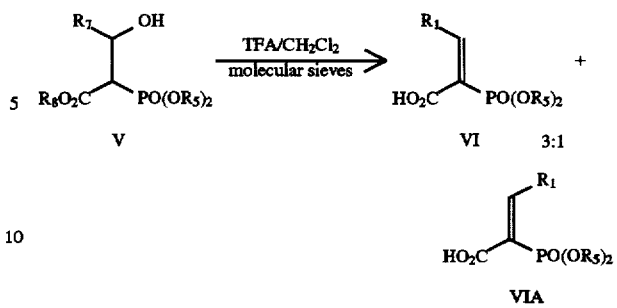

More particularly these processes may be accomplished by the following general procedures.

A general procedure for the Knovenagel condensation of tert-butyl O,O-dimethylphosphono acetate IV with aldehydes III is as follows. A 3-necked round bottomed flask is fitted with a nitrogen inlet, provisions for magnetic or mechanical stirring and a serum cap. The flask is then charged with anhyd. tetrahydrofuran (THF) and the solution is cooled to 0° C. in an ice/salt bath. Titanium tetrachloride (2 equivalents per aldehyde) is dissolved in carbontetrachloride and added dropwise to the THF solution. A Solution of the appropriate aldehyde (1 equivalent) III in a small amount of THF is then added to the above Solution followed by a solution of tert-butyl O,O-dimethylphosphono acetate (1 equivalent) IV in THF. Finally, N-methylmorpholine (4 equivalent) is added slowly to this stirring solution, after the addition is complete the solution is allowed to warm to room temperature and stirred for 24 h. The solution is then cooled to about 0° C. and treated with water dropwise over a few minutes. The solution is diluted with ether, poured into a separatory funnel and the aqueous phase extracted with ether 3 times. The combined ethereal solution is washed with $NaHCO_3$, brine, dried over anhyd. $MgSO_4$, filtered and concentrated in vacuo. The crude product, V and VA, is then purified by flash chromatography.

The general procedure for removal of a protecting group, such as the tert-butyl ester is as follows. A sample of the Knovenagel product, V and VA, is dissolved in dichloromethane and treated with an equal (volume) amount of trifluoroacetic acid at 0° C. The solution is allowed to warm to room temperature and the progress of the reaction monitored by TLC. When the reaction is finished the solvents are removed in vacuo and the residue purified by crystallization or flash chromatography on silica gel. This procedure produces the (Z) and (E)-2-substituted 1-carboxy-1-dimethoxyphosphono ethylene derivatives, VI and VIA. Curtius rearrangement of (E)-2-substituted 1-carboxy-1-dimethoxyphosphono ethylene derivatives Preparation of dehydro alpha-amino phosphonates is as follows. The (Z) and (E)-2-substituted 1-carboxy-1-dimethoxyphosphono ethylene derivatives, VI and VIA, and 1 equivalent of triethylamine is dissolved in dichloromethane and then treated with diphenylphosphoryl azide at 0° C. for a period of 1 h. The solution is then poured into a separatory funnel and washed with 1N $KHSO_4$, sat. aq. $NaHCO_3$, dried over anhyd. $MgSO_4$, filtered and concentrated in vacuo. The acyl azide thus produced is diluted with toluene and warmed to 90° C. for ca. 1 h to effect Curtius rearrangement. This solution is then treated with a mixture of triethylamine (1.5 equivalents) and benzyl alcohol (1.05 equivalents) and allowed to stir at 90° C. for an additional 1 h. The contents of the flask are then poured into a separatory funnel and washed with 1N $KHSO_4$, sat. aq.

NaHCO₃, brine, dried over anhyd. MgSO₄, filtered and concentrated in vacuo to give the desired dehydro alpha-amino acid, II, which was purified by flash chromatography over silica gel.

Variations in these conditions and evaluations for different compounds within the definitions of the formula are within the skill of an ordinarily skilled artisan. For example, substituents may include groups also recognized as requiring protective groups and, of course, these are readily prepared and removed as needed.

The compounds of the formula III and IV are known or can be prepared from compounds that are known by methods known in the art.

The catalytic asymmetric hydrogenation as described above for Scheme I is carried out on the dehydro alpha-amino phosphonate of the formula II in the presence of rhodium (R,R)-DiPAMP to produce the desired compound of the formula I.

When the appropriate corresponding starting materials are used the L-alpha-amino phosphonate analogue of phenylalanine is obtained in excellent yield with very high optical purity. The enantiomeric excess of this latter named reaction is found to be greater than 98%.

The following examples illustrate of the present invention processes using compounds of the above described processes. Various other compounds within the processes of the present invention are readily prepared by these or variations of these examples. That is, the following examples are not meant to be limiting.

EXAMPLE 1

Aminomethylenebis (phosphonic acid)

Formamide (54 g, 1.2 mol) is added dropwise to a solution of phosphorus acid (100 g, 1.2 mol) and phosphorus trichloride (500 g, 3.6 mol). The solution is warmed to 70° C. for 2 h and then diluted cautiously with 300 mL of water. The solution is then allowed to stand overnight and then concentrated on a rotary evaporator with the bath temperature at 90° C. Upon cooling, the solution solidifies and the product is isolated by filtration on a Buchner funnel. The filter cake is washed thoroughly with a mixture of methanol and water (1:1 v:v) and dried in vacuo to give 100 g, 44% of material with mp 255°–265° C.

N-[bis(Dimethoxyphosphoryl)methyl]formamide

A mixture of the aminomethylenebis(phosphonic acid) as prepared above (45 g, 0.39 mol), trimethyl orthoformate (250 g, 3.4 mol) and p-toluenesulfonic acid (2 g) are diluted with 500 mL of dry dimethylformamide and stirred at 120° C. for 2 days or until an appropriate assay indicates the reaction is complete. The solution is then filtered and concentrated in vacuo to give a semisolid. This material is recrystallized from acetone to give 64 g, 60% of material, mp 95° C.

N-[1(Dimethoxyphosphoryl)-2-phenylethenyl]formamide

A solution of N-[bis(dimethoxyphosphoryl)methyl] formamide (3.50 g, 12.7 mmol) is dissolved in 20 mL of dry methanol and treated with a solution of sodium methoxide (from 14 mmol of sodium metal) in methanol under nitrogen. The mixture is stirred at room temperature for 30 m and then treated with a solution of benzaldehyde (1.35 g, 12.7 mmol) in 5 mL of methanol. The solution is stirred at room temperature for 24 h and then concentrated in vacuo. The residue is extracted 3X with dichloromethane, the combined extracts dried over anhyd. MgSO₄, filtered, and concentrated in vacuo to give an oil that is purified by radial chromatography over silica gel eluting with dichloromethane to 10% methanol in dichloromethane. The appropriate fractions are combined and concentrated to give 2.31 g, 76% of the desired product as an oil.

Asymmetric hydrogenation of N-[1-{Dimethoxyphosphoryl)-2-phenylethenylformamide: Preparation of N-[1-(R)-(Dimethoxyphosphoryl)-2-phenylethyl]formamide A solution of N-[1-(Dimethoxyphosphoryl)-4-phenylethenyl]formamide (2.31 g, 9.7 mmol) is dissolved in 30 mL of degassed methanol in a Fisher-Porter bottle is treated with rhodium (R,R)-DiPAMP (50 mg, 0.067 mmol). The solution is flushed with nitrogen 5X and then with hydrogen 5X and hydrogenated at 40 psig for 16 h. The solution is then concentrated in vacuo and the residue purified by radial chromatography on silica gel eluting with 5% methanol in dichloromethane to give 1.00 g, 86% of material that is taken on the next step.

Hydrolysis of N-[1-(R)-Dimethoxyphosphoryl)-2-phenylethyl]formamide: Preparation 1(R)-amino-2-phenylethanephosphonic acid, (L-phosphono phenylalanine)

A solution of N-[1(R)-(Dimethoxyphosphoryl)-2-phenylethyl]formamide (500 mg, 2.1 mmol) in 40 mL of 6N HCl is heated to reflux for 48 h and then concentrated in vacuo. The residue is dissolved in ethyl acetate and water and treated with 1 mL of propylene oxide. The phases are separated and the aqueous phase extracted with ethyl acetate 3X. The combined ethyl acetate solution is dried over anhydrous MgSO₄, filtered, and concentrated to give 374 mg, 89% of a white solid, mp 264°–267° C., $[\alpha]_D @25°$ C.= –46 (c=0.5, 2N NaOH). IR(KBr) 1951, 1516 cm$^{-1}$. High resolution mass spectrum, calc'd for $C_8H_{12}O_3NP$: 202.0812. Found: 202.0633.

Knovenagel condensation of 4-benzyloxy benzyaldehyde with tert-butyl P,P-dimethylphosphonoacetate: preparation of 1-tert-butyl-1-dimethylphosphonyl-(E]-3-(4-benzyloxyphenyl) propenoate

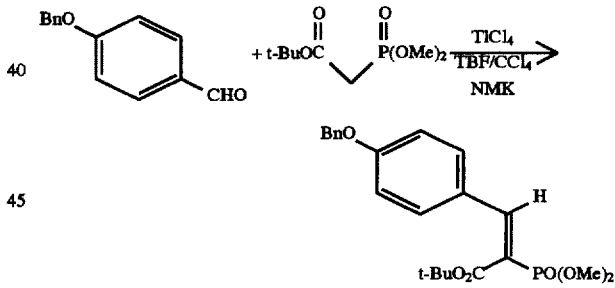

Procedure: a 2-neck, 500-mL, round bottom flask equipped with a nitrogen inlet and pressure-equalizing addition funnel is charged with THF (50 mL) and cooled in an ice bath. Titanium tetrachloride (8.46 g, d 1.750, 4.89 mL, 44.6 mmol) in CCl₄ (12 mL) is subsequently added dropwise via the addition funnel over 30 minutes resulting in the formation of a copious, yellow precipitate (TiCl₄·2THF). The 4-benzyloxybenzaldehyde (4.73 g, 22.3 mmol) in THF (8 mL) is added next via syringe over 5–10 minutes followed by the t-butyl P,P-dimethylphosphonoacetate (5.00 g, d 1.137, 4.40 mL, 22.3 mmol). N-methylmorpholine (9.02 g, d 0.920, 9.81 mL, 89.2 mmol) in THF (15 mL) is finally added via the addition funnel. The mixture is permitted to stir at 0° C. for 5 h before quenching with water (25 mL). The product is isolated by extracting the reaction mixture several times with ether. The combined ether layer is washed with saturated sodium bicarbonate and brine before drying over anhydrous magnesium sulfate. Filtration and evaporation of the solvent in vacuo revealed the crude product which is recrystallized from CH₂Cl₂/iso-octane to give 6.0 grams of white crystals (64% yield) 1-tert-butyl-1-dimethylphosphonyl-(E)-3-(4-benzyloxyphenyl) propenoate. $^1$H NMR: (CDCl₃, 300 MHz) δ 7.49 (m, 8H, aromatic and olefinic protons); 6.99 (d, J=8.9 Hz, 2H, p-subst. aromatic); 5.13 (s, 2H, benzyl CH₂); 3.84 (d, J=11.4 Hz, 2 eq. OCH₃'s split by P); 1.54 (s, 9H, t-butyl). $^{13}$C NMR: (CDCl₃, 75.6 MHz) δ 160, 147.5, 147,136, 131, 129, 128, 127, 126.7, 126.4, 115, 82.7, 70.1, 52.9 and 52.8 (P-OCH₃), 27.8. $^{31}$P NMR: (CDCl₃) δ 20.0. MS: (FAB) m/e (relative intensity) 425 [(M+Li)+, 5%], 369 [(M+Li-C₄H₈)+, 100%].

Selective deprotection of the tert-butyl ester: Preparation of 1-dimethoxyphosphonyl (E)-3-(4-benzyloxyphenyl) propenoic acid and 1-dimethyoxyphosphonyl (Z)-3-(4-benzyloxyphenyl) propenoic acid Procedure: The starting ester (3.7 g, 8.8 mmol) is dissolved in anhydrous dichloromethane (18 mL) under N₂.

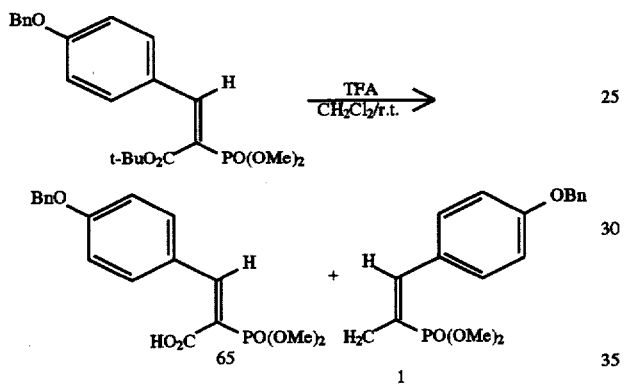

Trifluoroacetic acid (6.0 g, d 1.480, 4.1 mL, 53 mmol) is subsequently added dropwise at room temperature via syringe. The resulting red solution is permitted to stir overnight at room temperature. The solvent is then removed under reduced pressure, and saturated sodium bicarbonate is added to the residue. The aqueous layer is extracted several times with ethyl acetate to remove unreacted starting material before acidifying with conc. HCl. The carboxylic acid is subsequently extracted into ethyl acetate, and the ethyl acetate layer is washed with brine before drying over anhydrous magnesium sulfate. Filtration and evaporation of the solvent in vacuo revealed a bright yellow solid (2.85 g, 90% yield) which is identified as a mixture of olefins by proton NMR; the two isomers were not separated. $^1$H NMR for E-olefin: (CDCl₃, 300 MHz) δ 9.5 (br s, 1H, acid OH); 7.61 (overlapping pair of d's: J=8.8 Hz, 2H, p-subst. aromatic); 7.38 (m, 5H, aromatic); 6.98 (d, J=8.8 Hz, 2H, p-subst. aromatic); 5.10 (s, 2H, benzyl CH₂); 3.87 (d, J=11.4 Hz, 6H, 2 eq. OCH₃'s split by P). $^1$H NMR for Z-olefin: (CDCl₃, 300 MHz) δ 9.5 (br s, 1H, acid OH); 8.91 (d, J=42.3 Hz, olefinic proton); 7.76 (d, J=8.9 Hz, p-subst. aromatic); 7.38 (m, 5H, aromatic); 7.05 (d, J=8.9 Hz, p-subst. aromatic); 5.18 (s, 2H, benzyl CH₂); 3.75 (d, J=11.8 Hz, 6H, 2 eq. OCH₃'s split by P).

Formation of acyl azide: Preparation of dimethyl 1-azidocarbonyl 2 (E)-(4-benzyloxyphenyl) ethenephosprionate and dimethyl 1-azidocarbonyl 2(Z)-(4-benzyloxyphenyl) ethenephosphonate

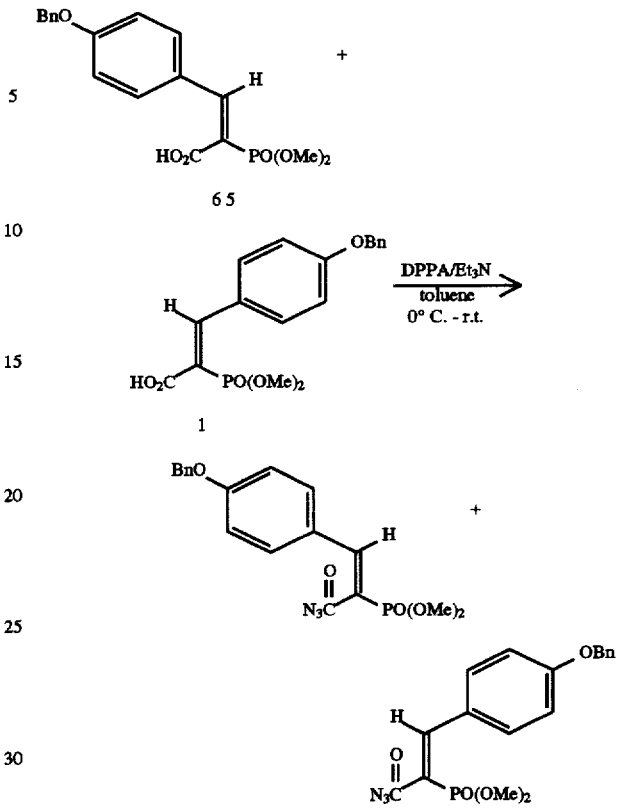

Procedure: To an ice-cooled solution of the acid mixture (2.73 g, 7.53 mmol) in dry toluene (11 ML) under nitrogen is added triethylamine (0.762 g, d 0.726, 1.05 mL, 7.53 mmol) and diphenylphosphoryl azide (2.07 g, d 1.277, 1.62 mL, 7.53 mmol). The resulting solution is stirred for 4 h at room temperature. The acyl azide products are isolated by diluting the solution with cold water and extracting with ether. The organic layer is dried over anhydrous magnesium sulfate, filtered, and evaporated under reduced pressure to reveal the crude product mixture which is immediately taken onto the next step.

Curtius rearrangement of acyl azide: Preparation of dimethyl 1-benzyloxycarbonylamino 2(E)-(4-benzyloxyphenyl) ethene phosphonate

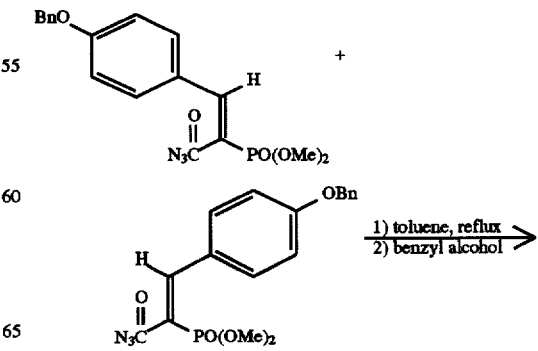

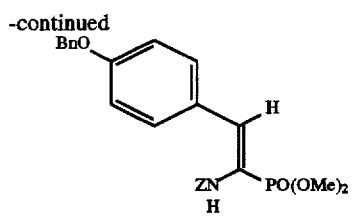

Procedure: The crude acyl azide mixture is redissolved in anhydrous toluene (11 mL), and the solution is heated to reflux under nitrogen. After heating for 1 h, benzyl alcohol (0.78 mL, 7.53 mmol) is added dropwise. The resulting mixture is permitted to stir overnight at reflux before diluting with ethyl acetate, washing with sat. NaHCO$_3$ (3 times), 1N HCl (2 times), and brine, and drying over anhydrous magnesium sulfate. Filtration and evaporation of the solvent in vacuo revealed an oil which is purified by flash column chromatography on silica gel initially using CH$_2$Cl$_2$ until the phenol by-product eluted, then switching to 1% MeOH/CH$_2$Cl$_2$ to elute the desired product (R$_f$=0.33, 5% MeOH/CH$_2$Cl$_2$). Recrystallization with CH$_2$Cl$_2$/iso-octane afforded a 56% yield of white crystals. $^1$H MMR: (CDCl$_3$, 300 MHz) δ 8 7.52 (d, J=8.8 Hz, 2H, p-subst. aromatic); 7.37 (m, 11H, aromatic and 1 olefinic); 6.92 (d, J=8.8 Hz, 2H, p-subst. aromatic); 5.92 (br s, 1H, NH); 5.14 (s, 2H, benzyl CH$_2$); 5.11 (s, 2H, benzyl CH$^2$); 3.78 (d, J=11 Hz, 6H, 2 eq. OCH$_3$'s split by P). $^{13}$C NMR: (CDCl$_3$, 75.6 MHz) a 160, 140.7, 140.3, 132, 128.6, 128.5, 128.2, 128.1, 127, 126, 115, 70.0, 67.5, 52.9 (d). MS: (FAB) m/e (relative intensity) 468 (MH+, 65% ); 359 (M+—PO(OMe)$_2$, (45%).

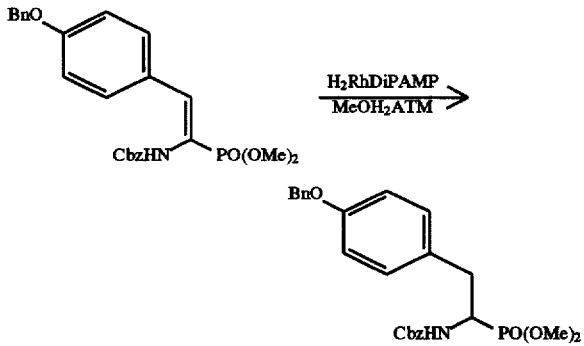

Asymmetric hydrogenation of dimethyl 1-benzyloxycarbonylamino 2(E)-4-benzyloxyphenyl) ethene phosphonate: Preparation of dimethyl (1(R)-benzyloxycarbonylamino 2-(4-benzyloxyphenyl) ethane phosphonate, (dimethyl N-Cbz-L-O-benzyl phosphonotyrosine)

Procedure: The starting material (700 mg, 1.5 mmol) and the rhodium (R, R) diPAMP catalyst (approximately 10–20 mg) are placed in a Fischer-Porter tube and flushed with nitrogen (5 times). Degassed methanol is subsequently added, and the tube is flushed 5 more times with nitrogen followed by 5 times with hydrogen before pressurizing to a final volume of 45 p.s.i. The reaction is then permitted to stir at room temperature for 40 h. Typically the chiral products are filtered through silica gel to remove the catalyst.

Preparation of dimethyl N-Cbz-L-phosphonoalanine

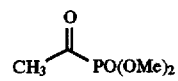

Dimethyl Acetylphosphonate. Trimethyl phosphite (57.1 g, 0.46 mol) is added dropwise to an ice cold solution of acetyl chloride (36.2, 0.26 mol) at a rate that the internal temperature did not rise above 5° C. The ice bath is removed and the solution warmed to room temperature and then heated to 100° C. for 1 hour. The solution is then vacuum distilled through a 12-inch Vigeraux column to give 30.87 g, 44% of a clear liquid with bp 57°–60° C. at 0.5 mm. H and C nmr are consistent with the assigned structure. This procedure is adapted from the published method of McConnell, R. L., Coover, H. W.,Jr. *J. Am. Chem. Soc.*, 1956, 78, 4450–4452.

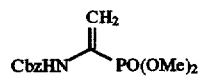

Preparation of Dimethyl 1-Benzyloxycarbonylamino-1-ethenephosphonate

Dehydrophosphonopeptide synthesis: Method A. A 250 mL round bottomed flask equipped with a reflux condenser is charged with dimethyl acetylphosphonate (15.2 g, 0.1 mol), benzyl carbamate (15.1 g, 0.1 mol) and 60 mL of dry toluene. The solution is then treated with 1 g of camphor sulfonic acid and then heated to reflux for 12 h. TLC on silica get eluting with 3:1 hexane:ethyl acetate shows the desired product is formed and had R$_f$=0.14. The solution is concentrated and purified by chromatography on a Prep-500 instrument with two silica gel cartridges eluting with hexane and ethyl acetate. The appropriate fractions are combined and concentrated to give 9.58 g, 31% of pure product that slowly crystallized on standing, mp 50°–52° C. This is essentially the method published by Zon, *J. Synthesis*, 1981, 324.

Dehydrophosphonopeptide synthesis: Method B. A solution of dimethyl acetylphosphonate (12.4 g, 0.081 mol), benzyl carbamate (12.33 g, 0.081 mol) and 260 mL of dry toluene is treated with phosphorus oxychloride (30.3 mL, 0.33 mol). The solution is then warmed to 70° C. for 1 h and then cooled to room temperature. The solution is then poured into a solutio of sat. aq. NaHCO$_3$, the pH of the solution is maintained between 6.9 and 7.3 by the addition of additional solid NaHCO$_3$. The phases are separated and the aqueous phase extracted with two 500 mL portions of ethyl acetate. The combined organic phase is dried with anhyd. MgSO$_4$, filtered, and concentrated in vacuo to give an oil 19.0 g, which was purified by chromatography on a Prep-500 as described above to give the pure product 7.7 g, 30%.

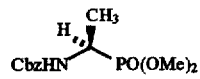

Asymmetric hydrogenation of N-Cbz-dehydrophosphonoalanine (Dimethyl 1(R)-Benzyloxycarbonylamino-1-ethanephosphonate): Preparation of N-Cbz-L-phosphonoalanine A Fischer-Porter bottle is charged with N-Cbz-dehydrophosphonoalanine (5.00 g, 16.0 mmol) in 20 mL of degassed methanol. To this solution is added rhodium (R,R)

DiPAMP (20 mg, 0.026 mmol). The solution is then flushed with nitrogen five times and then with hydrogen five times and hydrogenated t 40 psig for 4 h. The bottle is opened and the solution concentrated in vacuo to give an oil, 5.03 g, 100% of product that is purified by flash chromatography over silica gel to give 4.89 g, 97% of N-Cbz-L-phosphonoalanine as an oil. Evaluation of the optical purity of this product by chiral vapor phase chromatography on a Chirasil Val III 25 meter column revealed that 95% of the material was (R) and 5% was (S), for an enantiomeric excess of 90%.

Using analogous method with appropriate corresponding starting materials the following compounds are prepared using the processes of the present invention.

TABLE 1

| $R_1$ | $R_3$ | % Yield | % ee |
|---|---|---|---|
| H | $C_6H_5CH_2OCO$ | 95 | 90 |
| $C_6H_5$— | HCO | 86 | 100 |
| $C_6H_5$ | $C_6H_5CH_2OCO$ | 93 | 98 |
| p-$C_6H_5CH_2OC_6H_4$— | $C_6H_5CH_2OCO$ | 93 | 98 |
| $(CH_3)_2CH$ | $C_6H_5CH_2OCO$ | 97 | 88 |
| 1-naphthyl | $C_6H_5CH_2OCO$ | 97 | 98 |
| cyclohexyl | $C_6H_5CH_2OCO$ | 95 | 91 |

What is claimed is:
1. A compound of the formula (II)

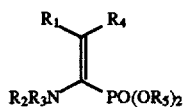

wherein $R_1$ is
(1) hydrogen;
(2) alkyl of from one to three carbons optionally substituted by one or two hydroxyl, chloro, or fluoro;
(3) cycloalkyl of from 3 to 7 ring carbons;
(4) phenyl optionally substituted by one to three substituent(s) consisting of
  (a) alkyl of from one to four carbons,
  (b) halogen consisting of fluoro, chloro, bromo, iodo,
  (c) alkoxy of from one to three carbons,
  (d) nitro,
  (e) amido,
  (f) mono- or di-alkyl (of from one to four carbons) amido;
  (g) hydroxy;
  (h) benzyloxy
(5) tolyl;
(6) tolyl, substituted by one to three substituents consisting of
  (a) alkyl of from one to four carbons,
  (b) halogen consisting of fluoro, chloro, bromo, iodo,
  (c) alkoxy of from one to three carbons,
  (d) nitro,
  (e) amido,
  (f) mono- or di-alkyl (of from one to four carbons) amido;
  (g) hydroxy;
(7) naphthyl optionally substituted by one to three substituents consisting of
  (a) alkyl of from one to four carbons,
  (b) halogen consisting of fluoro, chloro, bromo, or iodo,
  (c) alkoxy of from one to three carbons,
  (d) nitro,
  (e) amido,
  (f) mono- or di-alkyl (of from one to four carbons) amido,
  (g) hydroxy; or
(8) indol-3-yl, indol-2-yl, imidazol-4-yl;
(9) NHA where A is
  (a) trityl,
  (b) hydrogen,
  (c) alkyl of from one to six carbons,
  (d) $R_{10}CO$ wherein $R_{10}$ is (A) hydrogen, (B) alkyl of from one to six carbons optionally substituted with hydroxyl, chloro, or fluoro, (C) phenyl or naphthyl unsubstituted or substituted with one to three of (i) alkyl of from one to three carbons, (ii) halogen wherein halogen is F, Cl, Br, or I, (iii) hydroxy, (iv) nitro, (v) alkoxy of from one to three carbons, (vi) $CON(R_{11})_2$ wherein $R_{11}$ is independently hydrogen or alkyl of from one to four carbons, or (D) a 5 to 7 member heterocycle;
  (e) phthaloyl wherein the aromatic ring is optionally substituted by one to three of (i) alkyl of from one to three carbons, (ii) halogen where halogen is F, Cl, Br, or I, (iii) hydroxy, (iv) nitro, (v) alkoxy of from one to three carbons, (vi) $CON(R_{11})_2$ wherein $R_{11}$ is independently hydrogen or alkyl of from one to four carbons,
  (f) $R_{12}(R_{13}R_{14}C)_mCO$ wherein m is one to three and $R_{12}$, $R_{13}$, and $R_{14}$ are independently (A) hydrogen, (B) chloro or fluoro, (C) alkyl of from one to three carbons optionally substituted by chloro, fluoro, or hydroxy, (D) hydroxy, (E) phenyl or naphthyl optionally substituted by one to three of (i) alkyl of from one to three carbons, (ii) halogen where halogen is F, Cl, Br, or I, (iii) hydroxy, (iv) nitro, (v) alkoxy of from one to three carbons, (vi) $CON(R_{11})_2$ wherein $R_{11}$ is independently hydrogen or alkyl of from one to four carbons, (F) alkoxy of from one to three carbons, (G) 5 to 7 member heterocycle or (H) $R_{12}$, $R_{13}$, and $R_{14}$ are independently joined to form a monocyclic, bicyclic, or tricyclic ring system each ring of which is a cycloalkyl of from three to six carbons; except that only one of $R_{12}$, $R_{13}$ and $R_{14}$ can be hydroxy or alkoxy on the same carbon and cannot be hydroxy, chloro or fluoro when m is one;
  (g) $R_{12}(R_{13}R_{14}C)_mW$ wherein m is independently 1 to 3 and W is OCO or $SO_2$ and $R_{12}$,$R_{13}$ and $R_{14}$ are independently as defined above;
  (h) $R_{20}W$ wherein $R_{20}$ is a 5 to 7 member heterocycle selected from the group consisting of indolyl, pyridyl, furyl, and benziosoxazolyl;
  (i) $R_{21}W$ wherein $R_{21}$ is phenyl or naphthyl unsubstituted or substituted by one to three substituents of(i) alkyl of from one to three carbons, (ii) halogen where halogen is F, Cl, Br, or I, (iii) hydroxy, (iv) nitro, (v) alkoxy of from one to three carbons, (vi) $CON(R_{11})_2$ wherein $R_{11}$ is independently hydrogen or alkyl of from one to four carbons;
  (j) $R_{12}(R_{13}R_{14}C)_mP(O)(OR_{22})$ wherein $R_{22}$ is alkyl of from one to four carbons or phenyl and $R_{12}$, $R_{13}$ and $R_{14}$ are independently as defined above;
  (k) $R_{20}P(O)(OR_{22})$ wherein $R_{20}$ and $R_{22}$ are independently as defined above;
  (l) $R_{21}P(O)(OR_{22})$ wherein $R_{21}$ and $R_{22}$ are independently as defined above;
(10) $R_{12}(R_{13}R_{14}C)_mV$ wherein V is O or NH and $R_{12}$, $R_{13}$ and $R_{14}$ are independently as defined above;
(11) $N(R_{11})_2$ wherein $R_{11}$ is independently as defined above;

(12) $NR_{15}NR_{16}$ wherein $R_{15}$ and $R_{16}$ are joined to form a 4 to 6 membered saturated nitrogen containing heterocycle which is (i) azetidinyl, (ii) pyrrolidinyl, (iii) piperidinyl, or (iv) morpholinyl;

(13) $R_{17}OCH_2O$ wherein $R_{17}$ is
  (a) alkyl of from one to six carbons,
  (b) $R_{21}$ wherein $R_{21}$ is independently defined as above; or
  (c) $CH_2Q_1$ wherein $Q_1$ is phenyl, naphthyl or a 5 to 7 membered heterocycle as defined above;

(14) $R_{17}OCH_2CH_2OCH_2$ wherein $R_{17}$ is independently as defined above;

(15) alkynyl of from two to six carbons optionally substituted with $R_{21}$ wherein $R_{21}$ is independently as defined above;

(16) alkenyl of from two to six carbons optionally substituted with $R_{21}$ wherein $R_{21}$ is independently as defined above;

$R_2$ and $R_5$ are independently hydrogen, alkyl, lower cycloalkyl, or ar wherein ar is an aromatic group;

$R_3$ is a protecting group; and $R_4$ is hydrogen with the overall proviso that when $R_3$ is formyl and $R_5$ is methyl or ethyl then $R_1$ cannot be hydrogen, methyl, hexyl, phenyl or phenylethenyl; that when $R_3$ is benzoyl and $R_5$ is ethyl, then $R_1$ cannot be phenyl, 4-chlorophenyl or hydrogen; and that when $R_3$ is acetyl or benzyloxycarbonyl and $R_5$ is ethyl, then $R_1$ cannot be hydrogen: with the further proviso that when $R_3$ is [5-[2-chloro-4-(trifluoromethyl) phenoxyl]-2-nitrobenzoyl], and $R_5$ is hydrogen or isopropyl, then $R_1$ cannot be 4-fluorophenyl.

2. A compound of claim 1 wherein $R_1$ is cyclopentyl or cyclohexyl.

3. A compound of claim 1 wherein $R_1$ is phenyl substituted by one to three substituent(s) consisting of alkyl of from one to four carbons, halogen consisting of fluoro, chloro, bromo, iodo benzyloxy, alkoxy of from one to three carbons, nitro, amido, mono- or di-alkyl (of from one to four carbons) amido.

4. A compound of claim 1 wherein $R_1$ is tolyl or tolyl substituted by one to three substituents consisting of alkyl of from one to four carbons, halogen consisting of fluoro, chloro, bromo, iodo, alkoxy of from one to three carbons, nitro, amido, mono- or di- alkyl (of from one to four carbons), amido.

5. A compound of claim 1 where $R_1$ is naphthyl.

6. A compound of claim 1 wherein $R_1$ is 3,5-dimethyl-4-hydroxphenyl and $R_2$ and $R_5$ are hydrogen.

7. A compound of claim 1 wherein $R_3$ together with the N of formula II is a urethano.

8. A compound of claim 7 wherein the urethano is a group together with the nitrogen wherein the group is selected from a group consisting of carbalkoxy, para-methoxybenzyloxycarbonyl, or benzyloxycarbonyl.

9. A compound of claim 9 which is dimethyl 1-benzyloxycarbonylamino 2(E)-(4-benzyloxyphenyl) ethene phosphonate.

* * * * *